(12) United States Patent
Bulent et al.

(10) Patent No.: US 9,744,287 B2
(45) Date of Patent: Aug. 29, 2017

(54) PULSATILE FLOW BLOOD PUMP

(71) Applicants: Oran Bulent, Konya (TR); Oran Omer Faruk, Konya (TR); Avci Elif Oran, Konya (TR)

(72) Inventors: Oran Bulent, Konya (TR); Oran Omer Faruk, Konya (TR); Avci Elif Oran, Konya (TR)

( * ) Notice: Subject to any disclaimer, the term of this patent is extended or adjusted under 35 U.S.C. 154(b) by 214 days.

(21) Appl. No.: 14/412,200

(22) PCT Filed: Jul. 1, 2013

(86) PCT No.: PCT/TR2013/000250
§ 371 (c)(1),
(2) Date: Dec. 30, 2014

(87) PCT Pub. No.: WO2014/007785
PCT Pub. Date: Jan. 9, 2014

(65) Prior Publication Data
US 2015/0141911 A1    May 21, 2015

(30) Foreign Application Priority Data

Jul. 3, 2012 (TR) .............................. a 2012/07756

(51) Int. Cl.
| | |
|---|---|
| *A61M 1/36* | (2006.01) |
| *A61M 1/10* | (2006.01) |
| *A61B 5/0402* | (2006.01) |
| *A61B 5/021* | (2006.01) |
| *A61B 5/026* | (2006.01) |

(Continued)

(52) U.S. Cl.
CPC ........... *A61M 1/3666* (2013.01); *A61B 5/021* (2013.01); *A61B 5/026* (2013.01); *A61B 5/0402* (2013.01); *A61B 5/14542* (2013.01); *A61M 1/101* (2013.01); *A61M 1/1005* (2014.02); *A61M 1/3607* (2014.02); *A61M 1/3626* (2013.01);

(Continued)

(58) Field of Classification Search
CPC .. A61M 1/3626; A61M 1/3607; A61M 1/101; A61M 1/1015; A61M 1/1005
See application file for complete search history.

(56) References Cited

U.S. PATENT DOCUMENTS

| | | |
|---|---|---|
| 4,779,614 A | 10/1988 | Moise |
| 5,290,227 A | 3/1994 | Pasque |

(Continued)

FOREIGN PATENT DOCUMENTS

GB    2467133 A    7/2010

*Primary Examiner* — Leslie Deak
(74) *Attorney, Agent, or Firm* — Gokalp Bayramoglu

(57) ABSTRACT

The invention is about a next-generation blood pump that provides pulsatile blood flow, and has been developed for cardiopulmonary by-pass devices used for maintaining extracorporeal blood circulation during heart surgeries and the supportive devices of circulation system. This device is technically a sort of synchronous power-assisted motor employing direct driver technology. The mentioned blood pump contains a rotor rotating on a magnetic bearing without a shaft and through the helical wings placed into the rotor it provides pulsatile blood supply adequate for the body requirement synchronous with the ECG signals received from the patients. It provides a patient safer and controlled pulsatile blood flow while running at high efficiency.

14 Claims, 5 Drawing Sheets

(51) Int. Cl.
*A61B 5/145* (2006.01)
*A61B 5/1455* (2006.01)

(52) U.S. Cl.
CPC .... *A61B 5/14557* (2013.01); *A61M 2205/103* (2013.01); *A61M 2205/3303* (2013.01)

(56) References Cited

U.S. PATENT DOCUMENTS

| | | |
|---|---|---|
| 5,693,091 A | 12/1997 | Larson, Jr. |
| 5,820,579 A * | 10/1998 | Plotkin ............... A61M 1/3621 |
| | | 128/DIG. 3 |
| 5,879,375 A * | 3/1999 | Larson, Jr. ............ A61M 1/101 |
| | | 607/30 |
| 6,042,347 A | 3/2000 | Scholl |
| 6,053,705 A | 4/2000 | Schoeb |
| 2008/0221495 A1 * | 9/2008 | Steffens ................. A61M 1/10 |
| | | 604/4.01 |

* cited by examiner

PULSATILE FLOW BLOOD PUMP

TECHNICAL FIELD

The invention is about a next-generation blood pump that provides pulsatile blood flow, and has been developed for cardiopulmonary by-pass devices used for maintaining extracorporeal blood circulation during heart surgery and the supportive devices of circulation system. The mentioned pump is technically a sort of synchronous power-assisted motor employing direct driver technology.

It contains a rotor rotating on a magnetic bearing without a shaft and through the helical wings placed into the rotor it provides pulsatile blood supply adequate for the body requirement synchronous with the ECG signals received from the patients. As the interior surface of the pump that contacts with blood is small, it does not damage the shaped elements of the blood and provides a patient safer and controlled pulsatile blood flow while running at high efficiency.

PRIOR ART

The fact that the treatment methods except the surgery were inadequate for the treatment of congenital heart defects in 1940 and 1950s directed the pioneer heart surgeons to improve the techniques that enable to repair congenital heart defects. For the first time, Dr. John Gibbon performed a successful open-heart surgery on a young patient in 1953 using the extracorporeal circulation system successfully.

Basically, the cardiopulmonary by-pass devices consist of plastic pipes that enable circulation, a reservoir where venous blood accumulates, an oxygenator where blood is mixed with oxygen and a blood pump. The vein blood of the patient flows into the reservoir because of gravity with the help of a cannula placed into the right atrium or a large vein, then this blood is pumped into the oxygenator with a blood pump and then from there it is sent into the artery system through the cannula placed into the aorta. In this way, the patient is supported with an alternative circulation system as the heart stops during the heart surgery.

There have been various motors enabling blood circulation for many years for this purpose; centrifugal pumps, roller pumps and pulsatile flow pumps. Centrifugal pumps run with the help of concentric cones that rotate fast or an impeller. This impeller rotates the blood at high speed and the blood reaches to the pump outlet. A flow meter should be used to determine how much the blood flow is since the forwarded blood flow can be changed with the speed of pump and artery line afterload when centrifugal pumps are employed.

Thus, non-pulsatile blood flow is achieved. A clamp is attached on the artery line to prevent back flow when the pump is stopped, and there are also check valves. Centrifugal pumps may lead to less cavitation and microemboly while generating forward pressure.

Roller pumps run by compressing polyvinyl, silicon or latex tubes in one direction with cylindrical rollers placed inside. Two small cylinders, rotating in a rotary, pump the blood forward by squeezing the elastic tube. The flow of the pump is proportional with the speed of roller rotation and the diameter of the pipe placed inside. The caliber of the pipe set to be used in the pump inlet is the key determinant for the maximum blood flow to be achieved.

The others are the numbers of the length of the pipe while the rollers rotate and the cycle of the pump head per minute. Roller pumps are double-headed and had rotating heads. Blood is pushed forward by squeezing a wide thick tube in the main pump room. Thus, a non-pulsatile blood flow is achieved. The vulnerable points of the roller pumps can be mentioned as; cavitation of air occurrence in the head area, flow calibration that cannot be determined precisely, back flow resulting from inadequate occlusion, the risk of tear or burst of the line, and changeable compression of the head. The forward flow is not affected so long as there is no pressure in the outlet line.

The flow of the pump is directly proportional with the rotation speed and the diameter of the tube set placed inside it. Centrifugal pumps are superior to roller pumps in terms of two main points. Firstly, high back-pressure is not formed even if temporary obstruction occurs. Secondly, wide gas embolism does not occur even if there is tube compression.

BRIEF DESCRIPTION OF THE INVENTION

The invention is a blood pump that enables pulsatile blood flow and has been developed for the cardiopulmonary by-pass machines and blood circulation support devices. This pump consists of a rotor which has helical wings inside and rotates frictionlessly in a magnetic bearing but does not have a shaft and a stator that rotates it. Motor starts with systole and stops with diastole synchronic to the ECG signals received from the patient, and provides pulsatile blood flow.

The perfusion obtained through the pulsatile blood flow with blood pump provides vital hemodynamic advantages when compared with non-pulsatile perfusion. Pulsatile blood flow is the physiologic blood flow model in a healthy subject. Pulsatile blood flow in the circulation of the patient means extra energy transfer into the micro circulation, and this extra kinetic energy helps to deliver the erythrocytes to the capillaries.

Thus, it increases capillary circulation, helps lymph circulation, and as a result it affects cell metabolism positively. To sum up, the blood flow generated by a quality cardiopulmonary by-pass machine or a blood circulation support device should be pulsatile from now on.

Our invention, pulsatile blood pump, does not damage the shaped elements of blood, and provides safer and controlled pulsatile blood flow while running at high efficiency since its interior surface that contacts with blood is narrow. Furthermore, as the part that includes helical winglets is apart from the system and designed as a disposable plastic material another set will be used for each patient and there will be no risk for the infection.

Figure 1:
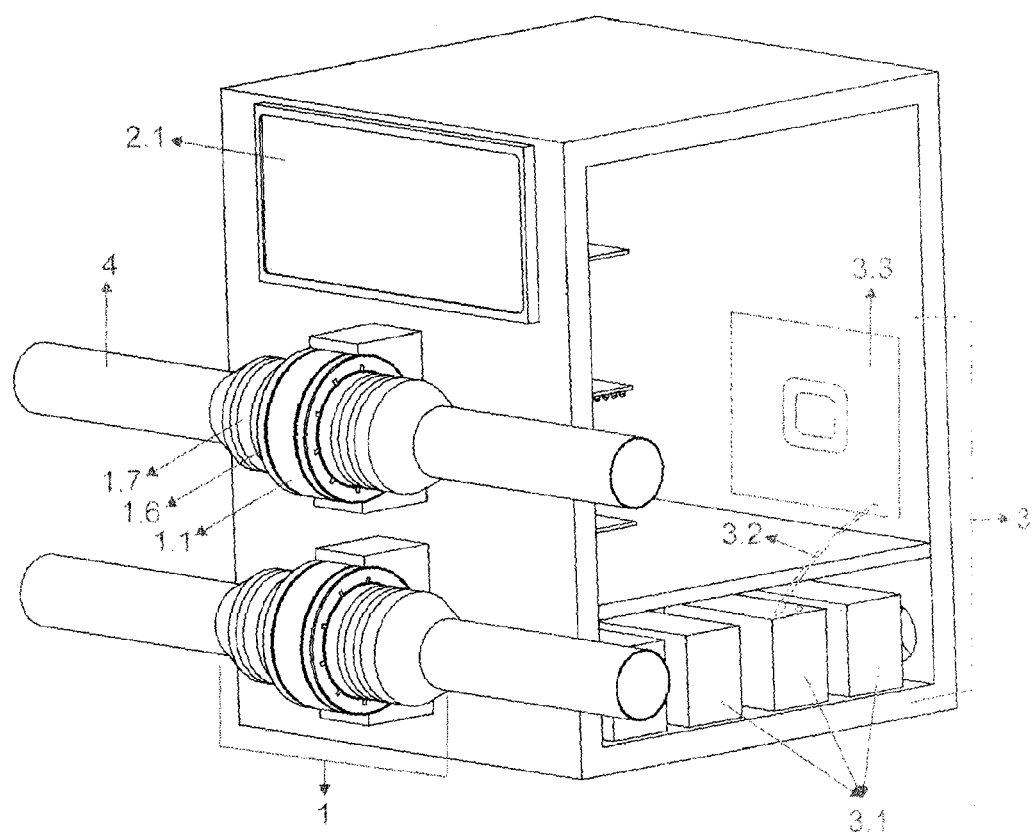
FIG. 1. General view of the Cardiopulmonary Pulsatile Blood Pump
Figure 2:
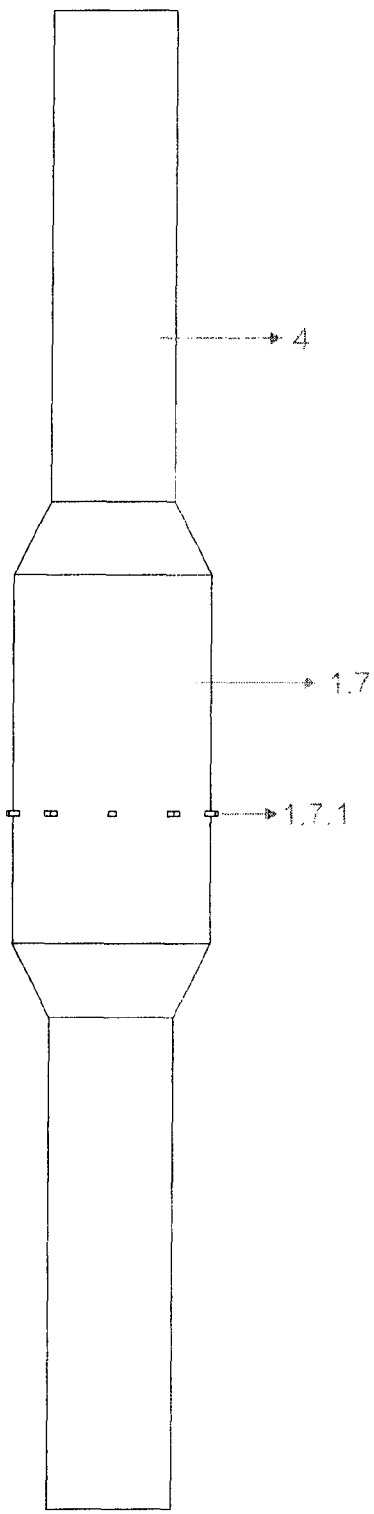
FIG. 2. General view of the Casing
Figure 3:
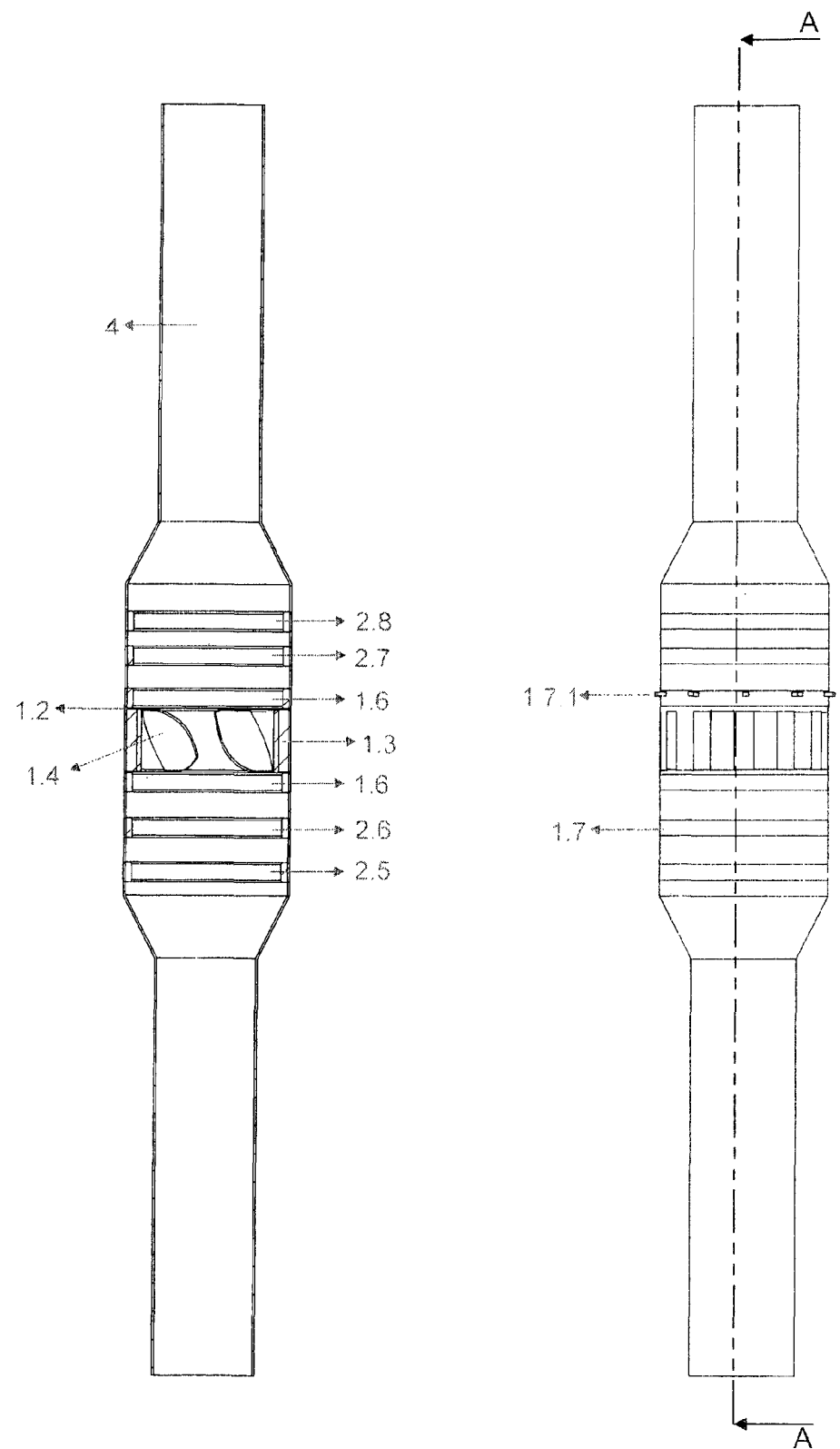
FIG. 3. Sectional view of the Disposable Part
Figure 4:
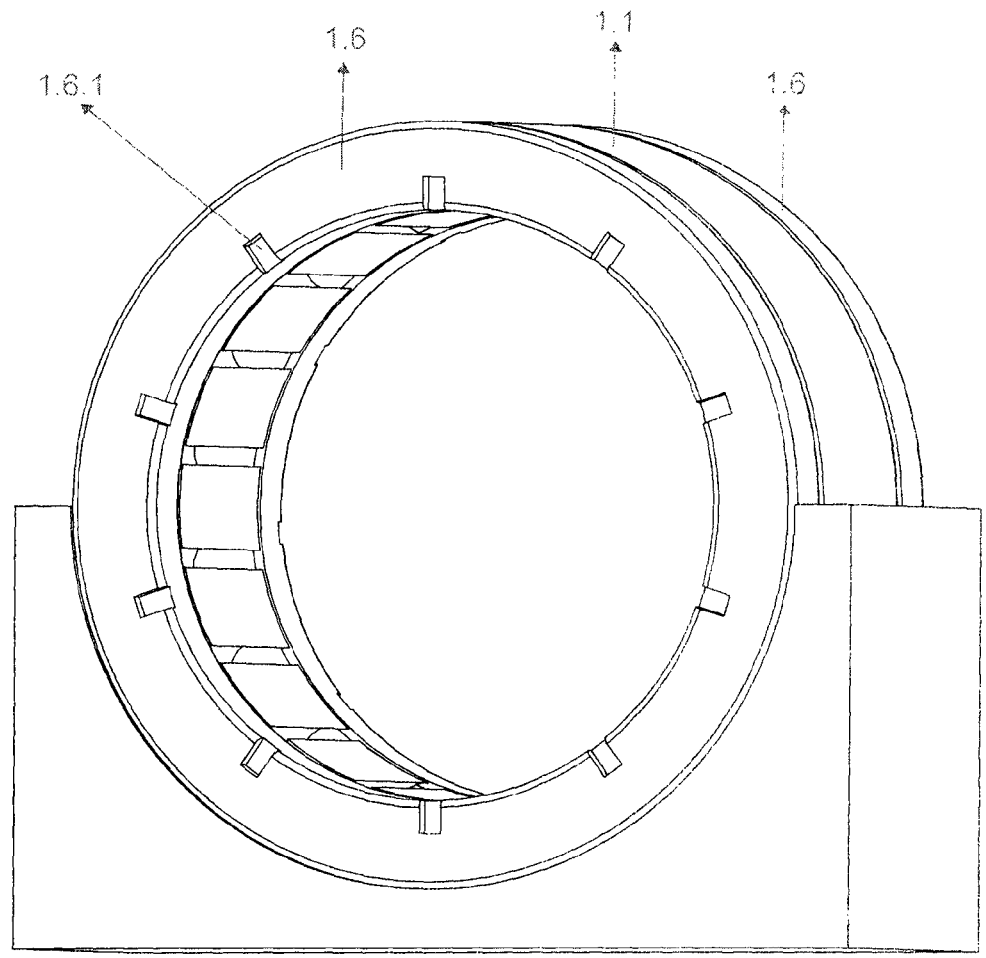
FIG. 4. The view of Stator and Permanent External Part
Figure 5:
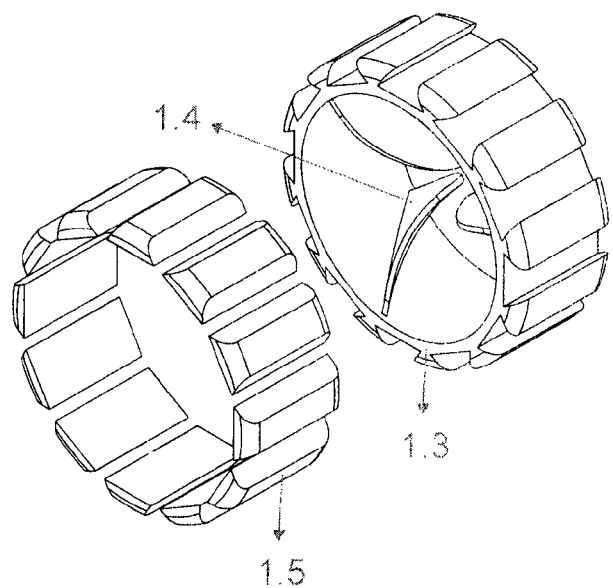
FIG. 5. The view of Exploded Rotor
Figure 6:
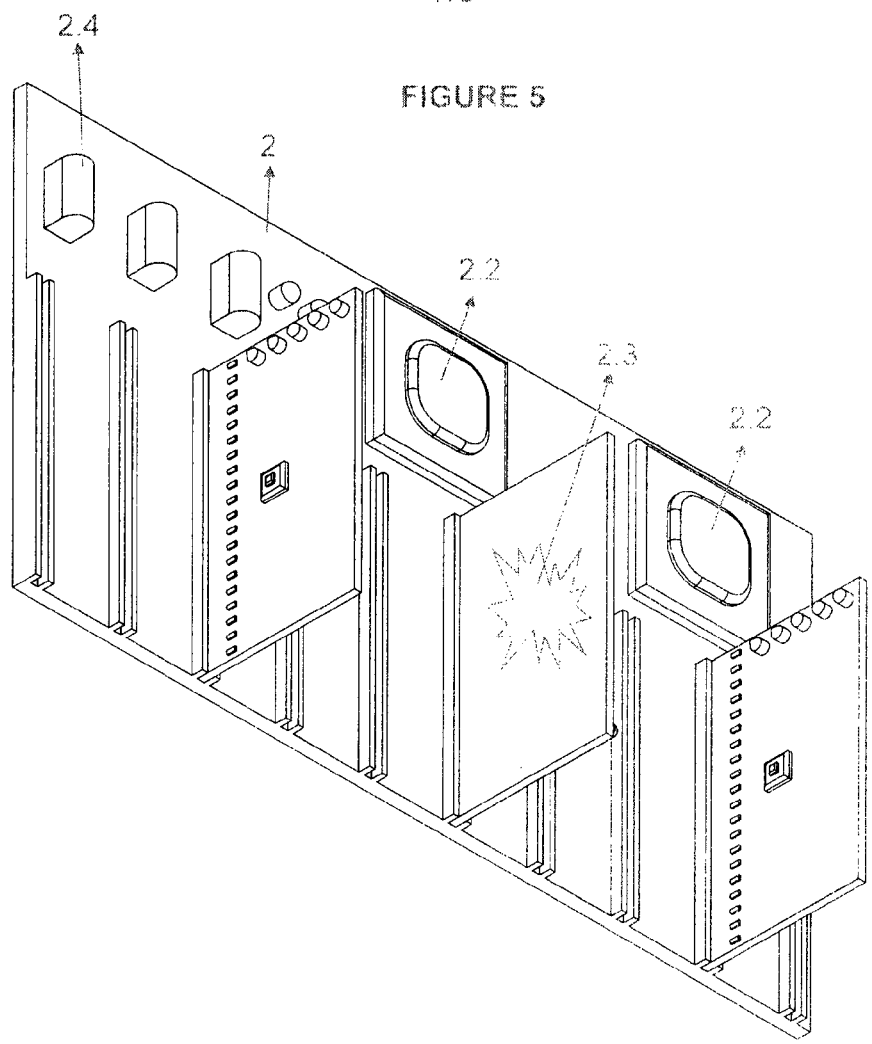
FIG. 6. The view of Control Units

The responses of the numbers in the figures of the parts are as follow:

1. Pulsatile blood pump
    1.1. Stator
    1.2. Magnetic Bearing
    1.3. Rotor
    1.4. Helical Winglet 1.5. Permanent Neodymium Magnet Bar
1.6. Permanent Neodymium Magnet Ring
  1.6.1. Magnetic Bearing Connecting Tab Seat
1.7. Casing
  1.7.1. Connecting Tab
2. Control Unit
  2.1. Touch Screen
  2.2. Microprocessor
  2.3. Software
  2.4. ECG Connection
  2.5. Pressure Sensor
  2.6. Flow meter
  2.7. Oxygen Saturation Sensor
  2.8. Air Cavitation Sensor
3. Power Unit
  3.1. Battery
  3.2. Power Cables
4. Uninterruptable Power Supply
5. Plastic Pipe

THE DETAILED DESCRIPTION OF THE INVENTION

The invention consists of a pulsatile blood pump (1), a control unit (2) and a power unit part (3). Pulsatile blood pump (1), stator (1.1), a hollow rotor rotating frictionlessly in a magnetic bearing in the stator (1.3), helical winglets fixed into the rotor (1.4), permanent neodymium magnet bars on the rotor (1.5), permanent neodymium magnet rings (1.6) on both sides of the stator and rotor, and a case made of biocompatible plastic material in which the parts that constitutes the interior surface of the pulsatile blood pump exist (1.7).

Control unit (2) consists of a touch screen (2.1) that makes it possible for the users to transfer the data and enables the users to switch insertion, a microprocessor (2.2) that is programmed with a software (2.3) and controls pulsatile blood pump (1) in order to maintain pulsatile blood flow, ECG connection (2.4), pressure sensors (2.5), blood flow sensors (2.6), oxygen saturation sensor (2.7), and air cavitation sensor (2.8). An electric motor consists of two cylindrical and coaxial parts; one stationary (stator) the other moving (rotor). Pulsatile blood pump consists of at least one rotor (1.1), a stator (1.3), permanent neodymium magnet bars (1.5) on the rotor and permanent neodymium magnet rings (1.6) on both sides of the stator (1.3) and a rotor (1.6). Stator (1.3) is outboard of the pulsatile blood pump. The stator (1.3), made of overlapped siliceous sheet metal, contains the electric coils that rotate rotor. The rotor (1.1), which has permanent neodymium magnet bars (1.5) on, made of biocompatible raw material, and is a hollow cylinder without a shaft, takes place inside. Pulsatile blood pump (1) runs with electric energy. When the system starts, also magnetic bearing (1.2) starts to rotate together with the helical winglets fixed into the rotor (1.3) thanks to the force caused by the electric coils. When the rotor (1.1) stops, it can remain frictionlessly in the magnetic bearing (1.2) formed with permanent neodymium magnet rings (1.6) on both sides of the stator and rotor, and the permanent neodymium magnet bars (1.5) on it. When the rotor starts, it rotates freely in the same magnetic bearing with the current sent to the electric motor coils in the stator (1.1). The helical winglets (1.4) fixed onto the interior surface of the hollow rotor (1.1) form completeness with cylindrical rotor (1.1), and propel blood by rotating with rotor (1.1). The interior surface of the pulsatile blood pump (1) that contacts with blood is much smaller than the other known systems. Consequently, there will be no damage on the shaped elements of blood and coagulation systems.

Control unit (2) regulates the pulsatile blood pump (1) operation. Control unit (2) is the place where ECG signals obtained from the patient, and the blood pressure and blood flow data received from the system are processed and it contains a special software (2.3). Moreover, the actual data of the study can be seen on the touch screen in the control unit, and it enables one to reset the system after entering the authorized user profiles when a doctor finds it necessary. The data obtained through the software in the system (2.3) are processed with the help of the microprocessor (2.2). Pulsatile blood pump (1) is monitored and run with real time by the microprocessor according to the highest and lowest values of blood pressure and blood flow pre-set by an authorized user. Thus, the pulsatile blood flow is achieved within the limits of the required blood pressure (systolic and diastolic) and cardiac outflow (liter/min) by the intermittently running motor. Power unit (3) consists of at least one battery (3.1) that supplies controlled electric energy, and power cables (3.2) that transfer energy flow to the system. Uninterruptable power supply (3.3) exists in the system in order to tolerate power cut or voltage changes. The motor (1) of the pulsatile blood pump is a kind of synchronic brushless servo motor as can be guessed. A microprocessor is required in order to run a sophisticated brushless motor. The microprocessor (2.2) in the control unit (2) performs this duty. The microprocessor (2.2) controls the pulsatile blood pump (1) elaborately. The EKG signals received from the patient through ECG connection (2.4), blood flow (2.6), and the data obtained from the pressure sensors (2.5) are transferred to the control unit (2) with real times. These signals are amplified with an amplifier and are read by the microprocessor (2.2) through ADC (Analog to Digital Converter). Microprocessor (2.2) provides the optimal blood flow by analyzing these signals and running the pulsatile blood pump (1) intermittently according to the stored data in the software (2.3).

The rotor (1.3) located in the case (1.7) made of biocompatible plastic material, the permanent neodymium magnet bars (1.5) and the permanent neodymium magnet rings (1.6) on both sides of the rotor (1.3) constitute the interior surface of the pulsatile blood pump (1).

This part has been designed as disposable so that it can be used individually by each patient. With the help of the beads (1.7.1) on the case (1.7), made of biocompatible plastic material and in the shape of a tube, it is caught in the bead seats on the permanent neodymium magnet rings (1.6) on both sides of the stator (1.1). Therefore, no user error risk appears. This disposable part has prominent sides to which plastic pipe sets of the system are attached firmly in the inlet and outlet of the pump.

It also has the software and equipment to display % oxygen saturation on the screen when a blood gas and oxygen saturation sensor (2.7) is logged into the system. In addition, when the existent air bubble cavitation sensor (2.8) indicates air bubbles, it stops the motor and switches on the alarm.

Considering the vital importance of the blood circulation of the patient, every piece of the parts in the system (stator, rotor, pressure sensor, flow sensor, ECG connection cable) is held stand*by for emergency and designed so that they can be replaced immediately if any technical problem arises. When a negative unexpected event occurs (i.e.: higher or lower voltage than the desired limits, power cut, low battery, air bubbles leakage into the system), audio and light alarm is switched on.

The invention claimed is:

1. A blood pump for providing pulsatile blood flow with cardiopulmonary by-pass devices and the supportive devices of circulation system, wherein the blood pump enables pulsatile blood flow by running systolic and diastolic intermittently like a healthy human heart, and comprises
 a pulsatile blood pump,
 wherein the pulsatile blood pump includes
  a rotor, wherein the rotor is a hollow cylinder without a shaft, the rotor having helical wings disposed inside the rotor,
  a stator that rotates the rotor,
  a magnetic bearing inside the stator, wherein the rotor rotates frictionlessly in the magnetic bearing; and
 a control unit;
 wherein the control unit comprises
  an ECG connection configured to provide an ECG data of a patient to the control unit,
  a pressure sensor configured to measure a blood pressure data,
  a blood flow sensor configured to measure a blood flow data,
  an oxygen saturation sensor configured to measure an oxygen level in the blood,
  an air cavitation sensor configured to detect presence of an air bubble in the blood,
  a microprocessor configured to receive and process the ECG data, the blood pressure data, the blood flow data and the oxygen level in the blood, and control functioning of the pulsatile blood pump accordingly.

2. The blood pump according to claim 1, wherein the pulsatile blood pump further comprises a plurality of permanent neodymium magnet bars on the rotor, a disposable biocompatible case with a plurality of beads, and a plurality of permanent neodymium magnet rings disposed on both sides of the rotor are placed in the case.

3. The blood pump according to claim 1, wherein the stator is made of overlapped siliceous sheet metal, and contains a plurality of cavities where a plurality of electric coils can be located.

4. The blood pump according to claim 1, wherein the pulsatile blood pump is a synchronic servo motor, and runs with low voltage.

5. The blood pump according to claim 1, wherein the control unit further comprises a touch screen, which enables users to input a user data;
 wherein the microcontroller is configured to use the user data to control the blood flow;
 wherein the microcontroller is further configured to display patient's statistics on the touch screen.

6. The blood pump according to claim 1, wherein the control unit enables a physician to adjust the heart rate, blood pressure and blood flow according to a predetermined data when an authorized user enters the predetermined data of a patient.

7. The blood pump according to claim 6, wherein the rotor speed is controlled by the microprocessor according to the adjustments determined special for the patient by the physicians when synchronous signals are not received from the ECG connection or it is technically unavailable or in disordered states.

8. The blood pump according to claim 1, wherein the pressure sensor measures the blood pressure in the artery with real time and then sends the feedback to the microprocessor.

9. The blood pump according to claim 1, wherein the blood flow sensor measures the blood flow in the artery with real time and then sends the feedback to the microprocessor.

10. The blood pump according to claim 1, wherein a software enables the pulsatile blood pump to achieve pulsatile blood flow with the microprocessor with real time synchronized with the ECG signals, blood flow and blood pressure data received from the patient.

11. The blood pump according to claim 1, wherein the microprocessor starts and stops pulsatile blood pump intermittently by processing the data that it gets from the software.

12. The blood pump according to claim 1, wherein the pulsatile blood pump further comprises an uninterruptible power supply that is switched on when there is power cut or disorders.

13. The blood pump according to claim 1, wherein the pulsatile blood pump further comprises an oxygen saturation sensor that displays % oxygen saturation on the touch screen.

14. The blood pump according to claim 1, wherein the pulsatile blood pump further comprises a cavitation sensor that warns physicians with audio-visual alarms and stops the pulsatile blood pump when air bubbles enter the system.

* * * * *